US006813050B2

(12) United States Patent
Chen et al.

(10) Patent No.: US 6,813,050 B2
(45) Date of Patent: Nov. 2, 2004

(54) ROTARY MIRROR ARRAY FOR FAST OPTICAL TOMOGRAPHY

(76) Inventors: Nanguang Chen, 264 Mt. Hope Rd., Mansfield Center, CT (US) 06250; Qing Zhu, 22 Michele La., Mansfield Center, CT (US) 06250

( * ) Notice: Subject to any disclaimer, the term of this patent is extended or adjusted under 35 U.S.C. 154(b) by 0 days.

(21) Appl. No.: 10/346,236

(22) Filed: Jan. 17, 2003

(65) Prior Publication Data

US 2004/0021922 A1 Feb. 5, 2004

Related U.S. Application Data

(60) Provisional application No. 60/350,330, filed on Jan. 18, 2002.

(51) Int. Cl.[7] .............................................. G02B 26/08
(52) U.S. Cl. ...................... 359/201; 359/203; 359/212; 359/900; 359/368; 250/234
(58) Field of Search ................................ 359/201–203, 359/298, 318–320, 900, 358, 399, 423; 600/443, 445, 473, 476; 356/450, 455, 456, 457, 501; 250/234–236

(56) References Cited

U.S. PATENT DOCUMENTS

| 4,538,181 | A | * | 8/1985 | Taylor ........................ 348/205 |
| 5,784,186 | A | | 7/1998 | Wang et al. |
| 5,907,423 | A | | 5/1999 | Wang et al. |
| 6,111,645 | A | | 8/2000 | Tearney et al. |
| 6,341,870 | B1 | | 1/2002 | Koch et al. |
| 6,407,872 | B1 | | 6/2002 | Lai et al. |

OTHER PUBLICATIONS

Su, "Achieving variation of the optical path length by a few millimeters at millisecond rates for imaging of turbid media and optical interferometry: a new technique", Optics Letters, May 15, 1997, v 22, n 10, p 665–667.

Lee et al, "Ultrahigh Scanning Speed Optical Coherence Tomography Using Optical Frequency Comb Generators", The Japan Society of Applied Physics, Aug. 15, 2001, part 2, n 8B.

Delachenal et al, "Robust and rapid optical low–coherence reflectometer using a polygon mirror", Optics Communications, Apr. 15, 1999, v 162, p 195–199.

\* cited by examiner

*Primary Examiner*—James Phan
(74) *Attorney, Agent, or Firm*—Bolegh J Skutnik; B J Associates

(57) ABSTRACT

A high speed, high duty cycle, linear, optical scanning device suitable for optical coherence tomography, optical coherence microscopy and confocal microscopy is presented. For the microscopy applications stable, periodic scanning is achieved by using a rotary mirror array, having a rotational symmetry and mirrors tilted at a small angle with respect to the rotational plane. The rotary mirror array is rotated at a constant speed. For the tomography application periodic modulation of the optical path-length of the reference beam is controlled by the rotation of the rotary mirror array.

15 Claims, 5 Drawing Sheets

ROTARY MIRROR ARRAY FOR FAST OPTICAL TOMOGRAPHY

DOMESTIC PRIORITY UNDER 35 USC 119(E)

This application claims the benefit of U.S. Provisional Application No. 60/350,330, filed Jan. 18, 2002 by the inventors, Nanguang Chen and Qing Zhu.

GOVERNMENTAL INTEREST

This invention was made under the Department of Defense Federal grant number DAMD17-01-1-0216, DAMD17-001-0217 and National Institute of Health NIH 1 R01 DE11154-03.

BACKGROUND

1. Field of the Invention

This invention relates to delay lines in optical coherence tomographic and optical Doppler tomographic systems, and dynamic focusing mechanisms in confocal microscopy and optical coherence microscopy.

2. Prior Art Statement

Confocal microscopy, optical coherence tomography (OCT), and optical coherence microscopy (OCM) are novel optical tomography techniques which are very useful for providing subsurface high-resolution imaging of samples (including but not limited to biological and medical samples). Confocal microscopy can achieve a sub-micron resolution and a penetration depth up to a few hundred microns. Optical coherence tomography can provide a spatial resolution up to a few microns and a penetration depth up to a few millimeters. Its advantages over confocal microscopy are the higher sensitivity due to signal enhancement by optical interferences, and a faster image acquisition rate because the axial scanning is obtained by an optical delay line in the reference arm, which is generally faster than traditional mechanical scanning stages. Optical coherence microscopy is a combination of confocal microscopy and optical coherence tomography. It uses a high numerical aperture lens to reduce the spot size of the focal point in order to obtain a better spatial resolution than OCT, and low coherence interferometry to reject multiple scattering lights. However, the axial scanning range is limited by a much shorter Rayleigh range. As a consequence, an additional translation stage is always needed to achieve adequate axial scanning range.

In many potential biomedical applications, the data acquisition speed is a critical issue in suppressing motion artifacts and acquiring high resolution four dimensional images (three spatial dimensions and one temporal dimension). Rapid delay lines are necessary to achieve fast OCT, while dynamic focusing mechanism instead of mechanical scanning stages is desirable for fast confocal microscopy and OCM.

A primitive delay line is a translating mirror, which is driven by a linear motor, an actuator, or a piezoelectric transducer (PZT). As the mirror moves back and forth along the path of the received optical signal, the power consumption required to generate acceleration will increase dramatically with frequency and scanning range. This is the reason that most commercially available linear motors and actuators can only provide a repetition rate around 30 Hz when a 2–3 mm scanning range is required. Although PZT can be driven at much higher frequencies, they can provide a limited scanning range. Resonant scanners have been demonstrated to achieve a frequency of 1,200 Hz and up to a 3 mm optical length difference. The drawback is that the optical path length change is a time-dependent sinusoidal function. As a result, Doppler frequencies of interference signals are depth dependent and vary within a wide range, which may cause difficulties in signal filtering and introducing more noises.

Sophisticated delay lines require complicated arrangements of mirrors, gratings and/or lenses, as well as precise alignment. Grating based delay lines have the flexibility to adjust group delay and phase delay independently. Repetition rates of 2,000 scans/second and 4,000 scans/second have been reported for such delay lines with a galvanometer (driven with a 1-kHz triangle waveform) and a 4-kHz resonant scanner, respectively. It appears that without using resonant scanners, the vibrational motion based mechanical scanning cannot readily achieve a speed high enough to meet real time data acquisition requirements. Rotating cubes, rotating roof prisms, and a combination of a polygonal mirror and a glass cube can scan up to 28.5 kHz. However, these methods suffer from rather low duty cycles and/or considerable nonlinearity of optical path length change.

Recently, an OCT system without any moving parts for depth scanning was proposed, and a high repetition scanning rate of 500 kHz was achieved in a scanning range of 25 mm by using optical frequency comb generators. However, the depth resolution (100 microns) and signal to noise ratio of this system needs to be improved. In addition, the cost of this system is high due the use of expensive components, such as gigahertz electronics and electro-optical modulators. Some fast delay lines are linear and can achieve several kHz scanning speed. However, they suffer from wavelength dependent group velocity dispersion.

A fast scanning device is necessary for high-speed microscopic imaging methods such as optical coherence tomography (OCT) and confocal microscopy. In an OCT system, axial scanning is generally achieved with a variable optical delay line, whose repetition rate determines the image acquisition speed. In a confocal microscope, angular scanning of collimated beam is transformed into lateral scanning of focus inside a sample. Conventional scanners cannot readily achieve kilohertz repetition speed at a reasonable cost and acceptable performances.

A widely used delay line for OCT is based on a grating and a scanning mirror that has a varying tilting angle, as disclosed in U.S. Pat. No. 6,111,645A (Tearney et al.). The reported axial scanning rate was 2 kHz. The use of a grating is critical for converting angular beam scanning into optical path length change. However, dispersion of the grating may degenerate the resolution of the system and cause problems when multiple wavelengths are needed for spectroscopic information. In addition, non-linearity in scanning speed is inevitable when resonant scanners are used for kilohertz repetition rates.

A 2.58 kHz reflectometer comprised of a rotating polygon mirror was disclosed in an article entitled "Robust and rapid optical low-coherence reflectometer using a polygon mirror" by Delachenal et al. (Optics Communications, 162 (1999) pp. 195–199). The high scanning speed comes at the cost of poor linearity and a low duty factor. The same problems are related to the optical delay line with a rotating cube that was disclosed in an article entitled "Achieving variation of the optical path length by a few millimeters at millisecond rates for imaging of turbid media and optical interferometry: a new technique" by Su (Optics Letters.22, (1997), pp. 665–667).

Recently, an OCT system without any moving parts for depth scanning was disclosed in an article entitled "Ultra-high scanning speed optical coherence tomography using optical frequency comb generators" by Lee et al. (Japanese J. of Applied Physics, Part 2, 8B, (2001), L878–880). A fairly high repetition scanning rate of 500 kHz was achieved in a scanning range of 25 mm by using optical frequency comb generators. However, the depth resolution (100 microns) and signal to noise ratio of this system cannot meet requirements for biomedical applications. In addition, the cost of this system is high due to the use of expensive components, such as gigahertz electronics and electro-optical modulators.

One example of linear scanning optical delay line was disclosed in U.S. Pat. Nos. 5,784,186A and 5,907,423A (Wang et al.). A helicoid reflecting mirror was used as a linear scanning line in an optical second-harmonic generation autocorrelator. The scanning speed was reported as 43.5 Hz. Fabrication of the spiral reflecting surface would be expensive when a high accuracy and high reflectivity are required.

Another example relates to two oppositely lying reflection means that was disclosed in U.S. Pat. No. 6,341,870B1 (Koch et al.). A movement of one mirror with respect to another of 45 microns is enough to results in a path length change of 2 mm. However, the overall path length and path length change are very sensitive to orientation of the incident beam with respect to the mirrors. Very accurate alignment and vibration control may be required.

A further example of another design relates to an optical path length scanner using moving prisms that was disclosed in U.S. Pat. No. 6,407,872B1 (Lai et al.). The design was tested with Zemax simulation but no experimental validation has been reported. It also has the dispersion problem associated with the use of prisms. In addition, such a device cannot be used as a scanning device in confocal microscopy.

A number features, which are necessary for enhanced utilization of these techniques commercially in medical and other applications include the following; ability to linearly change the optical path length or the linear axial scanning of the focus inside a sample in the several millimeter range; high scanning speeds without sacrificing quality; dispersion free operation; easy to align; high duty factors; robust to provide long lifetimes; and have a structure that is easy to fabricate and inexpensive compared to alternatives. The aims of the present invention are to provide these features.

SUMMARY AND OBJECTIVES OF THE INVENTION

It is an objective of the present invention to provide a device which at high speed can linearly change an optical path length up to several millimeters.

It is another objective of the present invention to provide a device which at a high scanning speed can do linear axial scanning of a focus inside a sample over a range of several millimeters.

It is still another objective of the present invention to provide a high speed, axially, linear scanning device which is dispersion free, easy to align, can be used at a high duty factor, easy to fabricate, low cost as well as being robust and having a long lifetime.

In one embodiment, an optical coherence tomography system comprises a radiation source generating a beam of radiation; a waveguide system, or a beam splitter, receptive of the beam of radiation which splits the beam of radiation into a sample beam and a reference beam and recombines the sample beam as a return sample beam and the reference beam as a return reference beam into a composite beam. A delay mechanism is receptive of the reference beam and introduces a relative time delay between the sample beam and the reference beam.

In another embodiment, an optical coherence microscopy system comprises a radiation source generating a beam of radiation. A waveguide system, or a beam splitter, is receptive of the beam of radiation and splits the beam of radiation into a reference beam and a sample beam and recombines the sample beam as a return sample beam and the reference beam as a return reference beam into a composite beam. The composite beam is indicative of the interference between the reference beam and the sample beam. A phase modulator is receptive of the reference beam for generating fringe signals and a dynamic focusing mechanism is receptive of the sample beam for scanning the focal point inside the sample. The reference beam may be blocked to reduce the optical coherence microscopy system to a confocal microscopy system.

An optical scanning mechanism, for optical delay or dynamic focusing is described. The optical scanning mechanism comprises a set of reflectors receptive of a signal wherein the reflectors are positioned at a prescribed angle with respect to a plane of motion and a device for causing linear or rotational relative motion between the set of reflectors and the signal toward the plane of motion.

Briefly stated, the present invention provides a high speed, high duty cycle, linear, optical scanning device suitable for optical coherence tomography, optical coherence microscopy and confocal microscopy is presented. For the microscopy applications stable, periodic scanning is achieved by using a rotary mirror array, having a rotational symmetry and mirrors tilted at a small angle with respect to the rotational plane. The rotary mirror array is rotated at a constant speed. For the tomography application periodic modulation of the optical path-length of the reference beam is controlled by the rotation of the rotary mirror array.

The above and other objects, features, and advantages of the present invention will become apparent from the following description read in conjunction with the accompanying drawings. In which like reference numbers in different drawings denote like items.

DETAILED DESCRIPTION OF PREFERRED EMBODIMENTS

Figure 1:
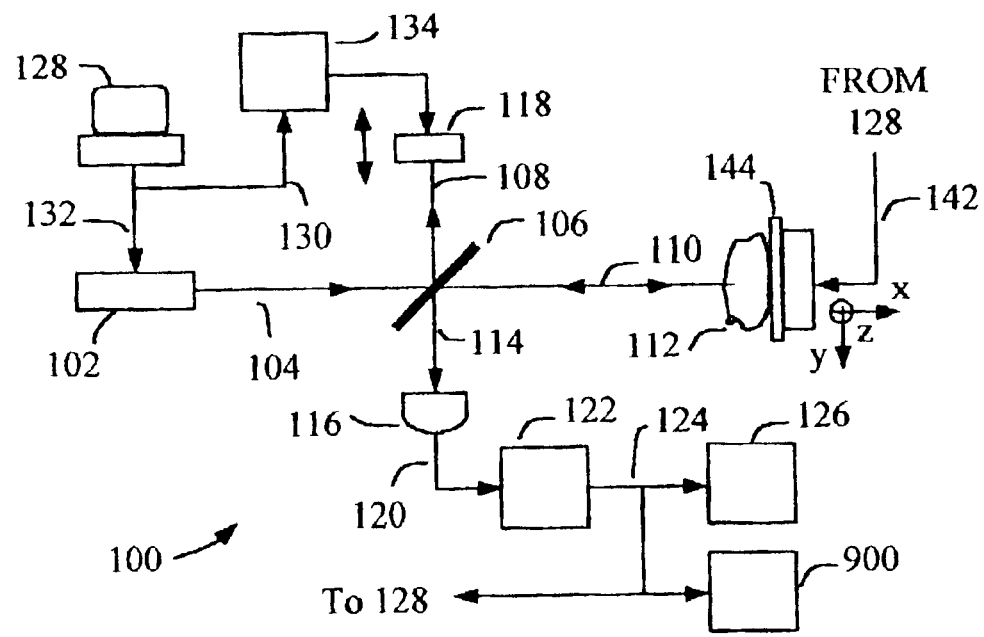
FIG. 1 is a schematic representation of a free space interferometer used in the present invention.

In FIG. 1 an optical coherence tomography (OCT) system is shown schematically at 100. The OCT system 100 comprises an interferometer including a light source 102 such as a superluminescent light emitting diode (SLED). The light source 102 generates a light beam 104 having a coherence length, $l_c$. The light beam 104 is directed to a beam splitter 106 which splits the light beam 104 into a reference beam 108 and a sample beam 110. The sample beam 110 is directed to a sample 112 such as a biological sample whereupon the sample beam 110 is reflected from the sample 112 and returned to the beam splitter 106. The reference beam 108 is directed to a signal delay mechanism 118 such as a rotary mirror array whereupon the reference beam 108 is reflected from the rotary mirror array 118 and returned to the beam splitter 106. At the beam splitter 106 the reference beam 108 and the sample beam 110 are combined into a composite beam 114 which is directed to a photodetector 116. The photodetector 116 converts the composite beam 114 into an electrical signal 120 indicative of the interference between the reference beam 108 and the sample beam 110. The electrical signal 120 is directed to a signal processing unit 122 for analyzing the interference between the reference beam 108 and the sample beam 110. The signal processing unit 122 provides as output a signal 124 which is directed to a monitor 126 or a computer or communications network 900 such as a local area network (LAN) or the internet. A motor 134 directs the rotation of the rotary mirror array 118 as will be described below. Also, a controller 128, receptive of the signal processing unit output signal 124, controls and coordinates the operation of the motor 134, the light source 102 and an X,Y,Z stage 144 by way of control signals 130, 132 and 142.

Figure 2:
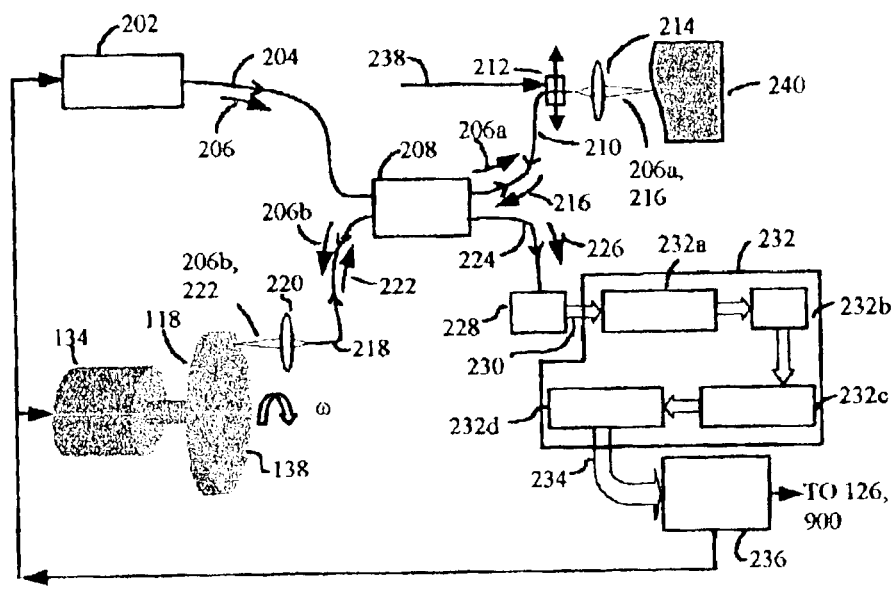
FIG. 2 is a schematic representation of a fiber optic based interferometer used in the present invention.

FIG. 2 shows a waveguide based OCT system at 200. The waveguide based OCT system 200 comprises a light source 202 such as a superluminescent light emitting diode (SLED) generating an input light beam 206 having a coherence length, $l_c$. The input light beam 206 is launched into an input optical fiber 204 for guidance there along. A device 208, such as a 2×2 coupler, for splitting the light beam 206 into two beams, receives the input light beam 206 from the input optical fiber 204 and conveys a portion of the input light beam 206 along a sample optical fiber 210 as a sample beam 206a, and along a reference optical fiber 218 as a reference beam 206b. Along the sample optical fiber 210, the sample beam 206a is guided to a lateral scanning mechanism 212, such as a galvanometer, and a lens set 214 whereupon the sample beam 206a is directed to a sample 240 such as a biological sample. The sample beam 206a encounters the sample 240 and is reflected there from as a return sample signal 216. The return sample signal 216 returns to the coupler 208 along the sample optical fiber 210. Along the reference optical fiber 218 the reference beam 206b is guided to a lens set 220 whereupon the reference beam 206b is directed to the rotary mirror array 118. The reference signal 206b is reflected from the rotary mirror array 118 as a return reference signal 222. The return reference signal 222 is guided back along the reference optical fiber 218 to the coupler 208 where it is combined with the return sample signal 216 as a composite beam 226. The composite beam 226 is thence guided along an output optical fiber 224 to a photodetector 228. The photodetector 228 converts the composite beam 226 into an electrical signal 230 indicative of the interference between the return reference beam 222 and the return sample beam 216 for signal processing at 232. In particular, the electrical signal 230 is amplified at 232a and then filtered at 232b. The electrical signal 230 is again amplified at 232c and converted into digital form at 232d. The digitized signal 234 is conveyed to a microprocessor or personal computer 236 which may perform additional A-line segmentation. The personal computer 236 is in turn connected to a monitor 126 or a computer or communications network 900 such as a local area network (LAN) or the internet. In addition, the personal computer 236 controls and coordinates the operation of the motor 134, the light source 202 and the lateral scanning device 212.

Figure 3:
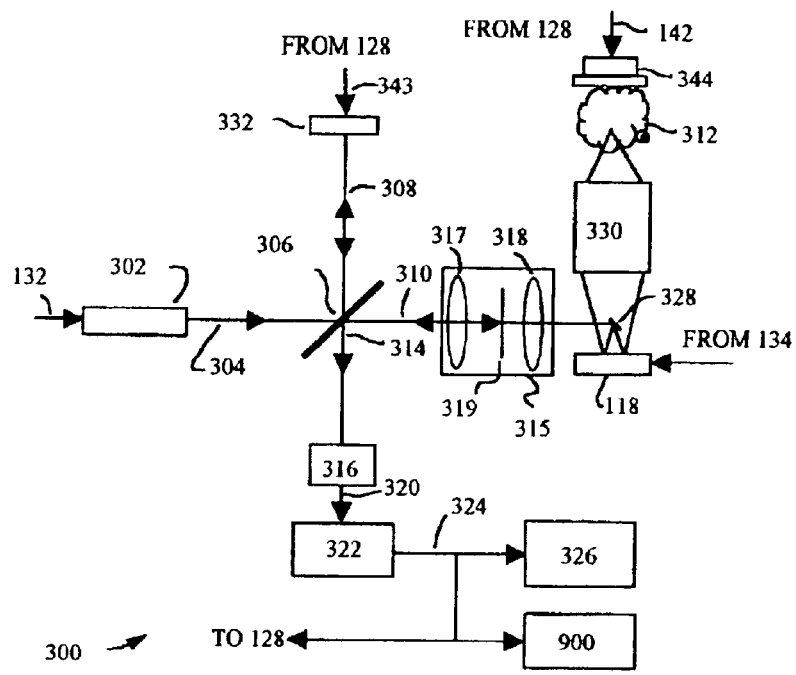
FIG. 3 is a schematic representation of a free space optical coherence microscope used in the present invention.

In FIG. 3 an optical coherence microscopy (OCM) system is shown schematically at 300. The OCM system 300 comprises an interferometer including a light source 302 such as a superluminescent light emitting diode (SLED). The light source 302 generates a light beam 304 having a coherence length, $l_c$. The light beam 304 is directed to a beam splitter 306 which splits the light beam 304 into a reference beam 308 and a sample beam 310. The sample beam 310 is directed to a spatial filter 315 comprising lenses 317, 318, and a pinhole 319, and is focused near a small mirror 328 whereupon the sample beam 310 is deflected to a dynamic focusing mechanism comprising the rotary mirror array 118 and a unitary telescope 330. The sample beam 310 is focused by the telescope 330 on to the sample 312 and returned all the way back to the beam splitter 306. The reference beam 308 is directed to a phase modulator 332 such as a mirror driven by a piezoelectric transducer (PZT) whereupon the reference beam 308 is reflected from the mirror and returned to the beam splitter 306. At the beam splitter 306 the reference beam 308 and the sample beam 310 are combined into a composite beam 314 which is directed to a photodetector 316. The photodetector 316 converts the composite beam 314 into an electrical signal 320 indicative of the interference between the reference beam 308 and the sample beam 310. The electrical signal 320 is directed to a signal processing unit 322 for analyzing the interference between the reference beam 308 and the sample beam 310. The signal processing unit 322 provides as output a signal 324 which is directed to a monitor 326 or a computer or communications network 900 such as a local area network (LAN) or the internet. As in FIG. 1, the motor 134 directs the rotation of the rotary mirror array 118 as will be described below. Also, the controller 128, receptive of the signal processing unit output signal 324, controls and coordinates the operation of the motor 134, the light source 302, the phase modulator 332 and an X,Y,Z stage 344 by way of control signals 130, 132, 343, and 142.

Figure 4:
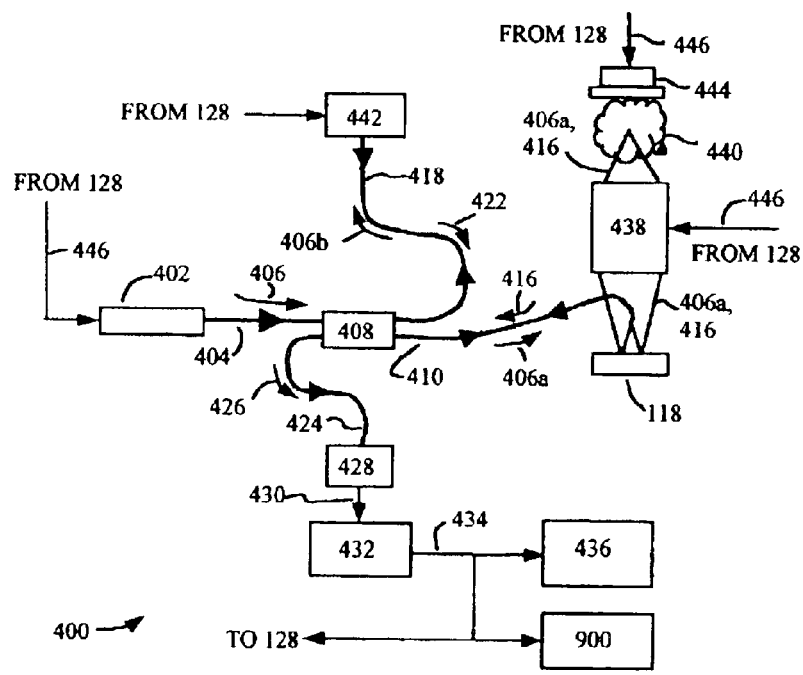
FIG. 4 is a schematic representation of a fiber optic based optical coherence microscope used in the present invention.

In FIG. 4 a waveguide based optical coherence microscopy (OCM) system is shown schematically at 400. The waveguide based OCM system 400 comprises an interferometer including a light source 402 such as a superluminescent light emitting diode (SLED). The light source 402 generates a light beam 406 having a coherence length, $l_c$. The output of the light source 402 is coupled into a single mode optical fiber 404, which is connected to the first port of a 2 by 2 optical coupler 408. The optical coupler 408 splits the input beam 406 into a reference beam 406b and a sample beam 406a. The sample beam 406a is directed by an optical fiber 410 to a dynamic focusing mechanism comprising the rotary mirror array 118 and a unitary telescope 438. The telescope 438 focuses the sample beam 406a on to the sample 440. The sample beam 406a is returned all the way back to the coupler 408 via the optical fiber 410 as a return sample beam 416. The reference beam 406b is directed by a second optical fiber 418 to a phase modulator 442 such as a mirror driven by piezoelectric transducer (PZT) whereupon the reference beam 406b is reflected from the mirror and returned to the coupler 408 via the second optical fiber 418 as a return reference beam 422. At the coupler 408 the return reference beam 422 and the return sample beam 416 are combined into a composite beam 426 which is directed to the forth port of the coupler 408 and from there to a photodetector 428 along optical fiber 424. The photodetector 428 converts the composite beam 426 into an electrical signal 430 indicative of the interference between the return reference beam 422 and the return sample beam 416. The electrical signal 430 is directed to a signal processing unit 432 for analyzing the interference between the return reference beam 422 and the return sample beam 416. The signal processing unit 432 provides as output a signal 434 which is directed to a monitor 436 or a computer or communications network 900 such as a local area network (LAN) or the internet. As in FIG. 1, the motor 134 directs the rotation of the rotary mirror array 118 as will be described below. Also, the controller 128, receptive of the signal processing unit output signal 434, controls and coordinates the operation of the motor 134, the light source 402, the telescope 438 and an X,Y,Z stage 444 by way of a set of control signals 446. The OCM system 400 may be reduced to a confocal microscopy system by blocking or removing the reference beam 406b. As best understood from FIG. 4, the sample 440 may be placed on a moveable X,Y,Z stage 444 in order to allow the sample beam 406a to scan the sample 440 while the telescope 438 is held stationary, or conversely, the stage 444 may be held stationary while the telescope 438 scans the sample beam 406a over the sample 440.

Figure 5:
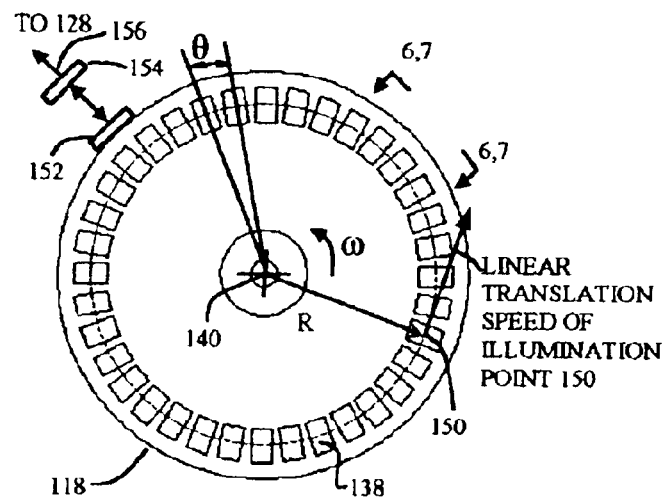
FIG. 5 is a frontal view of a rotary mirror array of the present invention as used in the interferometers of FIGS. 1 and 2.
Figure 6:
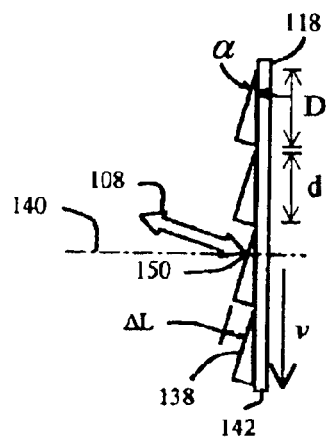
FIG. 6 is a sectional view of the rotary mirror array of FIG. 5.
Figure 7:
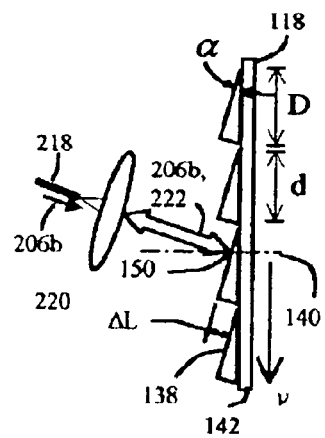
FIG. 7 is a sectional view of the rotary mirror array of FIG. 5 as used in the interferometer of FIG. 2.

The rotary mirror array 118 of FIGS. 1, 2, 3, 4, 8 and 10 is shown in greater detail in FIGS. 5, 6 and 7. The rotary mirror array 118 comprises a plurality of mirrors 138 circumferentially arrayed in a plane 642 and about a rotational axis 140. Under the direction of the motor 134, controlled by the controller 128, the rotary mirror array 118 is rotated about the rotational axis 140 at a prescribed rotational velocity, ω. The plurality of mirrors 138, receptive of the reference beams 108, 206b, thus rotate about the rotational axis 140 at the rotational velocity ω. The centers of the mirrors 138 are spaced apart from one another at a prescribed angular displacement, θ, and are located at a prescribed radius, R, from the rotational axis 140. As seen in FIG. 6, the mirrors 138 are also positioned or inclined at a prescribed angle, α, with respect to the local linear translation speed or with respect to the plane 642. The structure of the rotary mirror array is simple and symmetric, which makes it easy to fabricate. When the motor rotating at a constant speed, the electrical power consumed by the motor increases moderately with an increasing speed. However, it takes much more power to drive a vibrational device when the repetition rate goes up. In addition, high-speed vibrational motion can cause problems to the stability of the entire system.

In an OCT system, each mirror 138 is receptive of the reference beams 108, 206b at right angles thereto. To the linear approximation, as the mirrors 138 pass through or past the reference beams 108, 206b the delay or path difference, ΔL, between the reference beams 108, 206b and the sample beams 110, 206a varies according to the equation:

$$\Delta L = vt\sin\alpha + k \quad (1)$$

where k is a constant and v is the local linear velocity of the rotary mirror array 118 at the point 150 where the reference beam 108, 206b, 406b is incident upon each mirror 138. By taking the derivative with respect to time, t, we have the scanning speed, $$v_t = v\sin\alpha. \quad (2)$$

The repetition rate f, is inversely proportional to the spatial period D, $$f = v/D \quad (3)$$

When the mirror array 138 rotates at a constant speed, ω, the difference in optical path lengths, ΔL, of the two arms of the interferometers 100, 200 is modulated periodically and the linear translation speed at the point of illumination is v=ωR.

In each duty cycle, a more accurate expression of the one-way optical path length can be expressed as a function of time δt with the origin at the moment when the incident beam illuminates the center of the mirror, $$\Delta L = R\sin\alpha\sin(\omega\delta t) \quad (4)$$

-continued $$\approx R\sin\alpha\{\omega\delta t - (\omega\delta t)^3/6\}$$

Within each period, the change of optical path length, ΔL, is approximately a linear function of time. Although linear motion is a fairly good local approximation, small nonlinear terms result from the fact that circular motion is involved when a piece of mirror passes through the illumination point 150. Since the rotation angle ωδt is approximately in the range [−d/2R,d/2R], the relative nonlinear error is limited by a maximal value of nearly $d^2/24R^2$, where d is the width of the base of each mirror 138 in the moving direction and R is the distance from the rotational axis 140 to the center of each mirror 138. The relative nonlinear error value may be as small as 0.1% even with a duty factor close to 1. In contrast, most high-speed scanner such as rotary cubes suffers from a very low duty factor (typically a few percent) to keep approximate linear scanning.

In the reference arm 218, longitudinal scanning over a 2 mm range is achieved by the rotary mirror array 138. The mirrors are tilted at the angle of about 14 degrees with respect to the face 642 of the rotary base 118 and the direction of the local linear velocity. The equivalent radius R is about 50 mm, and the mirror spacing, D, is about 8 mm for each mirror. The rotary mirror array 138 may be driven by a brushless DC motor 134 or other suitable motor with a maximal rotation speed of 51,000 rpm. In the sample arm 210, a galvanometer 212 scans the light beam 206 laterally across the sample 240 to obtain 2-dimensional images. A 30 Hz sawtooth waveform drives the galvanometer 212 so that a B-scan, comprising 400 A-lines, can be acquired in about 0.033 seconds. Reflections from both arms 210, 218 superimpose in the output fiber 224 as an interference signal 226. The interference signal 226 is detected by a low noise photo detector 228 (e.g., D400FC, Thorlabs, Inc). A 100 MS/s ($10^8$ samples/sec) ultra high-speed data acquisition card is used to digitize the signal amplified by low noise amplifiers 232c. Further signal processing and A-line segmentation are conducted on a personal computer. A reflective optical sensor 154, together with a mark 152 on the periphery of the rotating base 118, is used to generate feedback signals 156 for timing purposes, as seen in FIG. 5. The timing signals are further processed in the computer so as to accurately indicate start point of one A-line. Continuous A-lines within two consecutive timing signals are segmented evenly with respect to the number of mirrors on the rotary mirror array. To achieve accurate segmentation, it is essential to maintain a stable rotation speed and high-resolution timing signals.

The ultrafast OCT system was tested with some simple imaging targets such as glass plates and transparency films. It was found that the spatial resolution of the system was almost identical to the coherence length of the light source 102, 202. This means that the fast delay line has no negative effect on the axial resolution. The interference signals 114, 226 have a center frequency of about 39 MHz, independent of the depth of axial scanning. No noticeable nonlinear effect has been observed. A fairly high duty cycle of 94% has been measured, which is in good agreement with the theoretical prediction. A repetition scan rate of 12 kHz over a 2 mm range has been achieved. A rotational speed of 30,000 revolutions per minute is typical for high-speed DC motors. This speed corresponds to 500 rotations per second. If, for example, there are 36 mirrors in the array, this corresponds to 18,000 A-lines generated per second. This is desirable for many clinical applications such as cardiac imaging, for which a frame rate of 30 frames per second is necessary. If 400 A-lines are required for one two-dimensional image, a total of 12000 A-lines need to be acquired in one second. Such a speed, together with requirements on spatial resolution, linearity, and duty factor, is not achievable with existing scanning devices.

The fast scanning delay line of the present invention has many advantages over existing technologies. First of all, video rate image acquisition has been achieved with minimal energy loss. Secondly, the frequencies of interference signals are depth independent and limited in a relatively narrow band, which warrant narrow bandpass filtering. These features can be exploited in optical Doppler tomography. Thirdly, the duty cycle of this system is high. Fourthly, the design is simple and easy to implement. The simplicity also improves the system robustness and alleviates burdens on maintenance. Fifthly, setting up and maintaining high-speed rotation is much more energy efficient than vibrating devices. Mechanical vibrations and noises can also be reduced. Finally, the mirror-array based delay line doesn't suffer from group velocity dispersion, which is desirable for retaining the system spatial resolution.

Figure 8:
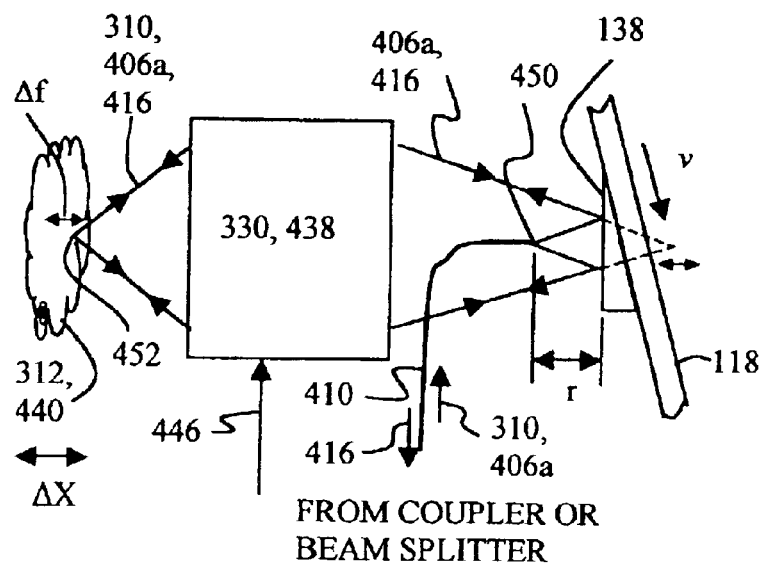
FIG. 8 is a sectional view of the rotary mirror array of the present invention as used in an OCM system of FIGS. 3 and 4.
Figure 10:
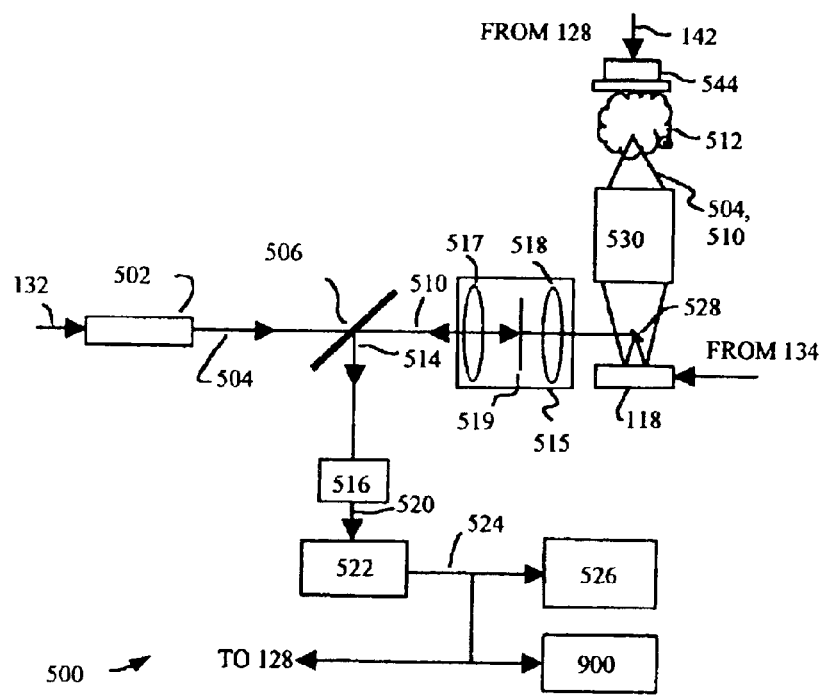
FIG. 10 is a schematic representation of a confocal microscopy system used in the present invention.

The rotary mirror array 118 used in the OCM system of FIGS. 3, 4 and 10 is shown in detail in FIG. 8. The sample beam 310, 406a is directed to an effective source point 450 close to the rotary mirror array 118 (a few millimeters, for example) by either the focusing lens 318 and a small mirror 328 as in FIG. 3, or the optical fiber 410 as in FIG. 4. The sample beam 310, 406a from this point is reflected by a mirror 138 of the rotary mirror array 118, and is directed to the telescope 330, 438 whereupon the sample beam 310, 406a is focused on to the sample 312, 440. The location of the focal point 452 within the sample 312, 440 depends linearly on the distance, r, between the effective source point 450 and the mirror 138 of the rotary mirror array 118. When the rotary mirror array 118 rotates steadily, the focal depth, Δf, within the sample 312, 440 is scanned periodically along the axial direction ΔX. The optical path length from the focal point 452 within the sample 312, 440 to the effective source point 450 can be made constant by the use of the unitary telescope 330, 438. The return sample beam 310, 416, from the sample 312, 440, returns all the way back to the effective source point 450 and thence returns to the coupler 408 via optical fiber 410, or to the beam splitter 306. At the coupler 408 or the beam splitter 306 the return sample beam 310, 416 combines with the return reference beam 308, 422 which has been modulated by the phase modulator 332, 442 to generate the composite beam 314, 426. The composite beam 314, 426 is detected by the photodetector 316, 428. The OCM system 300, 400 can achieve better spatial resolution than an OCT system 100, 200 by using high numerical aperture lenses in the telescope 330, 438. High image acquisition rates are feasible with the rotary mirror array 118.

Figure 9:
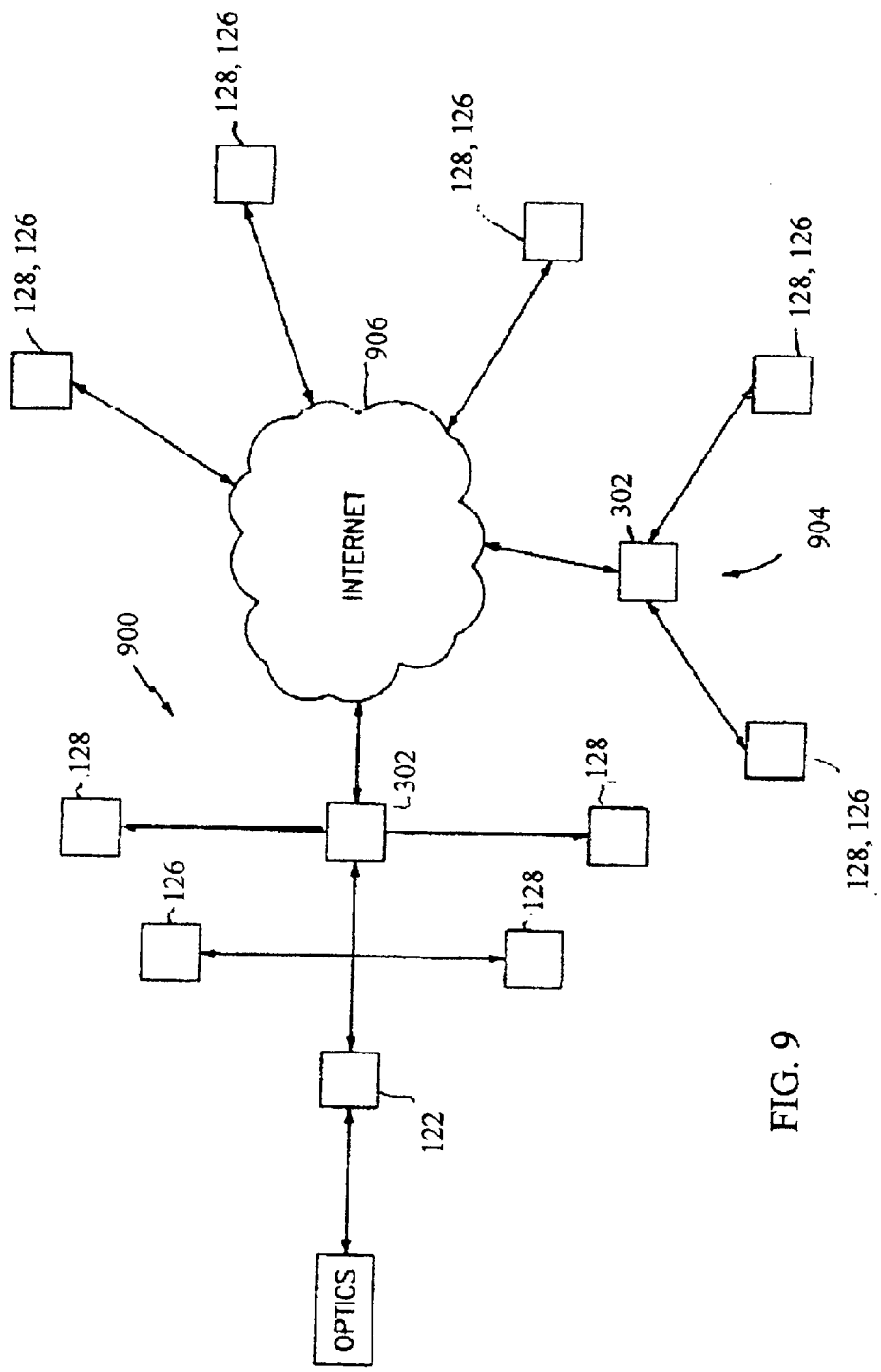
FIG. 9 is a schematic representation of a computer or communications network used in the present invention.

As seen in FIG. 9, the network 900 is a distributed computer or communications network, such as a local area network (LAN) or a wide area network (WAN), a global network (e.g. the Internet) or an intranet. The computer network 900 includes at least one other similar client personal computer 128 or display device 126 connected to a server 902 from remote geographical locations by wired or wireless connections, by radio based communications, by telephony based communications, or by other network-based communications. The computer 128 or display device 126 may also be connected directly to other like computers 128 or to display devices 126. The computer network 900 is in turn similarly connected to other computers 128, display devices 126 or networks 904 through the Internet 906. The computers 128, display devices 126 and other electronic media devices of the networks 900, 904 may be configured to execute computer program software, that allows them to send, receive, record, store and process commands or algorithms between and amongst themselves via the networks 900, 904 and the Internet 906 to image or to interferometrically sample biological or other types of samples and to generate tomographic images thereof. Such processing of the commands or algorithms includes, for example, various types of encryption, decryption, image compression and decompression algorithms, as well as other types of filtering, contrast enhancement, image sharpening, noise removal and correlation for image classification.

The OCM system may be reduced to a confocal microscopy (CM) system by blocking or removing of the reference beam as seen generally at 500 in FIG. 10. The CM system 500 comprises a light source 502 such as a light emitting diode (LED) or a laser diode (LD). The light source 502 generates a light beam 504. The light beam 504 is directed through a beam splitter 506. The light beam 504 continues to a spatial filter 515 comprising lenses 517, 518, and a pinhole 519, and is focused near a small mirror 528 and deflected to a dynamic focusing mechanism comprising the rotary mirror array 118 and an objective lens 530. The light beam 504 is focused by the objective 530 on to the sample 512 and returned all the way back to the beam splitter 506 as a return signal 510. At the beam splitter the return signal 510 is directed to photodetector 516. The photodetector 516 converts the return signal 510 into an electrical signal 520 indicative of the image of the sample 512. The electrical signal 520 is directed to a signal processing unit 522 for analyzing the image of the sample 512. The signal processing unit 522 provides as output a signal 524 which is directed to a monitor 526 or the computer or communications network 900 such as a local area network (LAN) or the internet. As in FIG. 1, the motor 134 directs the rotation of the rotary mirror array 118 as will be described below. Also, the controller 128, receptive of the signal processing unit output signal 524, controls and coordinates the operation of the motor 134, the light source 502 and an X,Y,Z stage 544 by way of control signals 130, 132, and 142.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as a data signal transmitted, whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

Thus, based upon the foregoing description an optical coherence tomography system, an optical coherence microscopy system and a confocal microscopy system have been disclosed. These systems comprise a radiation source generating a beam of radiation; a waveguide system receptive of the beam of radiation for splitting the beam of radiation into a sample beam and a reference beam and recombining the sample beam as a return sample beam and the reference beam as a return sample beam into a composite beam. An optical scanning mechanism, acting as a delay line, is receptive of the reference beam (or sample beam) for introducing a relative time delay between the sample beam and the reference beam. A dynamic focusing device axially scans the focal point inside the sample while keeping the optical path length constant. The system further comprises a photodetector receptive of the composite beam generating thereby an electrical signal indicative of the interference between the return sample beam and the return reference beam. In lieu of the waveguide system a beam splitter receptive of the beam of radiation splits the beam of radiation into a reference beam and a sample beam and recombines the reference beam and the sample beam into the composite beam which is indicative of the interference between the reference beam and the sample beam.

Also disclosed in the above description is an fast optical scanning mechanism comprising a set of mirror reflectors receptive of a signal wherein the reflectors are positioned at a prescribed angle with respect to a plane of motion; and a device for causing relative motion between the set of reflectors and the signal toward the plane of motion.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A high speed, high duty cycle, linear, optical axial scanning device, comprising:

a rotary mirror array having a number of small planar mirrors mounted on a rotary plane at a tilting angle;

a rotary motor operating at constant speed which drives said rotary mirror array;

said rotary mirror array having a discrete rotational symmetry about a revolutionary axis for said array;

an optical input port directing a beam onto said rotary mirror array;

an optical output port which collects said beam reflected from said rotary mirror array;

wherein said beam travels an optical path between said input port and said output port; and said optical path of said beam is subjected to periodic axial modulation.

2. The scanning device according to claim 1, wherein said beam is a reference beam, and said periodical modulation of said optical path is a variation in said path's length creating a linear optical delay line.

3. The scanning device according to claim 2, wherein said optical delay line is a component of an optical coherence tomography system.

4. The scanning device according to claim 1, wherein said beam is a probe beam, and said periodical modulation of said optical path is an axial scanning of said beam across a sample.

5. The scanning device according to claim 4, which further comprises:

focusing means, positioned after said rotary mirror array, to provide a focal point of said probe beam into a sample;

wherein said rotary mirror array deflects said probe beam onto said focusing means; and wherein said focal point is axially scanned inside said sample and said focusing means also directs scattered light from said sample off said rotary mirror array to said output port.

6. The scanning device according to claim 5, wherein said focusing means is selected from the group consisting of an objective lens, a telescope and a combination of both.

7. The scanning device according to claim 5, wherein said axial scanning device is a component in a confocal microscopy system.

8. The scanning device according to claim 1, wherein said beam is a sample beam, said sample beam optical path has a constant path length, and said periodical modulation of said optical path is a periodical axial scanning of a focal point of said sample beam.

9. The scanning device according to claim 8, which further comprises:

a sample arm along which said sample beam travels and a reference arm on which a reference beam travels;

a unitary telescope between said rotary mirror array and a sample;

wherein said rotary mirror array deflects said sample beam onto said telescope; and, wherein said telescope focuses said sample onto said sample and directs back scattered light from said sample off said rotary mirror array to said output port.

10. The scanning device according to claim 9, wherein said axial scanning device is a component in an optical coherence microscopy system.

11. The scanning device according to claim 10, further comprising a phase modulator in said reference arm.

12. The scanning device according to claim 1, wherein said optical input port and said optical output port are a single optical fiber.

13. The scanning device according to claim 1, wherein said optical input port and said optical output port are a subsystem comprising a combination of a lens and a small mirror.

14. An A-line segmentation method comprising the steps of:

a. positioning a marker on the periphery of a rotary mirror array;

b. positioning a reflective optical sensor near the periphery of the said rotary mirror array;

c. rotating said rotary mirror array at a constant speed;

d. obtaining timing signals from the said reflective sensor; and, e. segmenting continuous A-lines with said timing signals.

15. The segmentation method according to claim 14, which forms a central aspect of using an analysis technique selected from the group consisting of confocal microscopy and optical coherence microscopy.

* * * * *